United States Patent

Taub

[11] Patent Number: 4,626,545
[45] Date of Patent: Dec. 2, 1986

[54] AMINO ACID DERIVATIVES AS ENZYME INHIBITORS

[75] Inventor: David Taub, Metuchen, N.J.

[73] Assignee: Merck & Co., Inc., Rahway, N.J.

[21] Appl. No.: 644,188

[22] Filed: Aug. 27, 1984

[51] Int. Cl.$^4$ .................... A61K 31/40; C07D 207/08; C07D 207/12

[52] U.S. Cl. ..................................... 514/423; 548/530; 548/531; 548/533; 548/536; 548/540; 560/27; 560/37

[58] Field of Search .................. 548/540; 514/423

[56] References Cited

U.S. PATENT DOCUMENTS

| | | | |
|---|---|---|---|
| 4,052,511 | 10/1977 | Cushman et al. | 546/226 X |
| 4,129,571 | 12/1978 | Ondetti et al. | 546/221 X |
| 4,154,960 | 5/1979 | Ondetti et al. | 514/929 X |
| 4,206,122 | 6/1980 | Natarajan et al. | 548/540 X |
| 4,374,829 | 2/1983 | Harris et al. | 514/21 |

Primary Examiner—Joseph Paul Brust
Attorney, Agent, or Firm—Salvatore C. Mitri; Michael C. Sudol

[57] ABSTRACT

Compounds of the formula

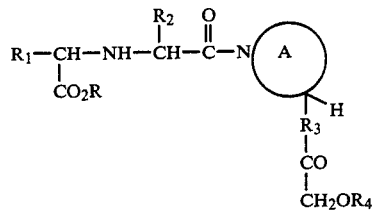

and their use as angiotensin converting enzyme inhibitors and antihypertensives are disclosed.

4 Claims, No Drawings

AMINO ACID DERIVATIVES AS ENZYME INHIBITORS

BACKGROUND OF THE INVENTION

The present invention is concerned with certain dipeptides as antihypertensive agents.

U.S. Pat. Nos. 4,129,571 and 4,154,960 disclose non-peptide, substituted acyl derivatives of amino acids which are useful as angiotensin converting enzyme inhibitors. More specifically, these compounds are mercapto substituted acyl amino acids and derivatives thereof including the clinically effective antihypertensive compound, captopril, i.e., D-3-mercapto-2-methyl-propanoyl-L-proline. These compounds contain an essential sulfhydryl substituent or derivative thereof whereas those of the present invention do not.

U.S. Pat. Nos. 4,374,829 discloses dipeptide angiotensin converting enzyme inhibitors of the formula $$R^1-CH-NH-CH-\overset{R^2}{\underset{\underset{O}{\|}}{C}}-Z-COOR$$
$$\underset{COOR}{|}$$

wherein the Z—COOR group includes the heterocycle proline.

U.S. Pat. No. 4,052,511 discloses N-carboxyalkanoyl-amino acids which are useful as angiotensin converting enzyme inhibitors.

Dipeptides of the above formula wherein the terminal group bonded to Z is $R_3$—CO—$CH_2OR_4$ rather than COOR have been discovered.

SUMMARY OF THE INVENTION

Compounds of the formula

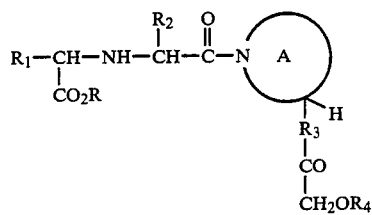

and their use as antihypertensive agents.

DETAILED DESCRIPTION OF THE INVENTION

An embodiment of the present invention is a compound of the formula

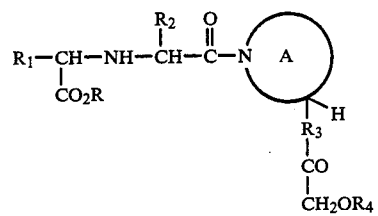

and pharmaceutically acceptable salts thereof, wherein
R is
  hydrogen;
  loweralkyl of $C_1$–$C_8$;
  aryl of $C_6$–$C_{12}$;
  arloweralkyl wherein the alkyl is $C_1$–$C_8$ and the aryl is $C_6$–$C_{12}$;
$R_1$ is
  hydrogen;
  hydrocarbon of from 1 to 12 carbon atoms which include branched and unsaturated hydrocarbon groups;
  $C_3$–$C_{10}$ cycloalkyl;
  substituted loweralkyl of $C_1$–$C_8$ wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino wherein the alkyl groups are $C_1$–$C_8$ and the aryl groups are $C_6$–$C_{12}$;
  substituted loweralkylamino of $C_1$–$C_8$ wherein the substituent can be halo, hydroxy, alkoxy of $C_1$–$C_8$ or cyano;
  arloweralkylamino wherein the alkyl is $C_1$–$C_8$ and the aryl is $C_6$–$C_{12}$;
  aryloxy wherein the aryl is $C_6$–$C_{12}$;
  arylthio wherein the aryl is $C_6$–$C_{12}$;
  aralkyloxy wherein the aryl is $C_6$–$C_{12}$;
  aralkylthio wherein the alkyl is $C_1$–$C_8$ and the aryl is $C_6$–$C_{12}$;
  benzofused cycloalkyl or bicycloalkyl of from 8–12 carbon atoms;
  aryl or heteroaryl wherein the aryl is $C_6$–$C_{12}$ containing an O, N or S heteroatom and which may be mono-, di- or trisubstituted by loweralkyl of $C_1$–$C_8$, hydroxy, loweralkoxy of $C_1$–$C_8$, halo, amino, acylamino, loweralkylthio of $C_1$–$C_8$ or aminoloweralkyl of $C_1$–$C_8$;
  arloweralkyl wherein the alkyl is $C_1$–$C_8$ and the aryl is $C_6$–$C_{12}$;
  arloweralkenyl wherein the alkenyl is $C_2$–$C_8$ and the aryl is $C_6$–$C_{12}$;
  heteroloweralkyl and heteroloweralkenyl in which the aryl or heteroaryl rings are $C_6$–$C_{12}$ containing an O, N or S heteroatom and which may be mono-, di- or tri-substituted by halo, loweralkyl of $C_1$–$C_8$, hydroxy, loweralkoxy of $C_1$–$C_8$, amino, loweralkyl of $C_1$–$C_8$, diloweralkylamino of $C_1$–$C_8$, aminoloweralkyl of $C_1$–$C_8$, acylamino, carboxy, haloloweralkyl of $C_1$–$C_8$, nitro, cyano or sulfonamido;
  substituted aralkyl or substituted heteroaralkyl wherein the alkyl is $C_1$–$C_8$ and the aryl is $C_6$–$C_{12}$ containing an O, N or S heteroatom and which include branched loweralkyl groups of $C_1$–$C_8$ wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido wherein the alkyl groups are $C_1$–$C_8$ and the aryl groups are $C_6$–$C_{12}$;
  any of the arloweralkyl or alkenyl and heteroloweralkyl or alkenyl groups described above in which the aryl or heteroaryl ring is partially or completely hydrogenated;
  substituted loweralkyl having the formula $R_A{}^1(CH_2)_n$—Q—$(CH_2)_m$ wherein n is 0–2, m is 1–3, $R_A{}^1$ is aryl or heteroaryl of $C_6$–$C_{12}$ containing an O, N or S heteroatom optionally substituted by amino, lower-dialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy wherein the alkyl groups are $C_1-C_8$, and Q is O, S, SO, $SO_2$, N—$R_B^1$, $CONR_C^1$, $NR_C^1CO$, CH=CH wherein $R_B^1$ is hydrogen, loweralkyl, aryl, aralkyl, loweralkanoyl, or aroyl wherein the alkyl groups are $C_1-C_8$ and the aryl groups are $C_6-C_{12}$, and $R_C^1$ is hydrogen, or loweralkyl of $C_1-C_8$;

$R_2$ is
hydrogen;
loweralkyl of $C_1-C_8$;
aminoloweralkyl $C_1-C_8$;

$R_3$ is $(CH_2)_n$ wherein n is 0, 1 or 2;

$R_4$ is
hydrogen;
loweralkanoyl of $C_1-C_8$;
arloweralkanoyl of $C_1-C_8$ and the aryl group is $C_6-C_{12}$;

the

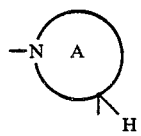

moiety is:

(a) a 5 to 11 membered N-heterocycle of the formula

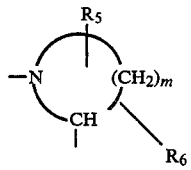

wherein m is 3-9;

$R_5$ and $R_6$ are independently selected from
hydrogen;
loweralkyl of $C_1-C_6$;
aryl of $C_6-C_{12}$;
substituted aryl of $C_6-C_{12}$ wherein the substituent can be loweralkyl of $C_1-C_8$, hydroxy, loweralkoxy of $C_1-C_8$, halo, amino, acylamino, loweralkythio of $C_1-C_8$ or aminolower alkyl of $C_1-C_8$;
arloweralkyl of $C_1-C_8$ and the aryl is $C_6-C_{12}$;
substituted loweralkyl of $C_1-C_8$ wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, or acylamino;
halogen;
amino;
methylene; alkylamino of $C_1-C_8$;
aralkyl amino wherein the alkyl is $C_1-C_8$ and the aryl is $C_6-C_{12}$;
X-$R_7$, wherein X
is O, S, NH, C=O or C=S and $R_7$ is H, loweralkyl of $C_1-C_8$, aryl of $C_6-C_{12}$, alkylamino of $C_1-C_8$, aralkyl amino wherein the alkyl is $C_1-C_8$ and the aryl is $C_6-C_{12}$;
loweralkyl of $C_1-C_8$;

hydroxyloweralkyl of $C_1-C_8$;
loweralkenyl of $C_2-C_8$;
hydroxyloweralkenyl of $C_2-C_8$; and, COOR wherein R is as defined above;

(b) a bicyclic derivative of a 5 or 6 membered N heterocycle having the formula

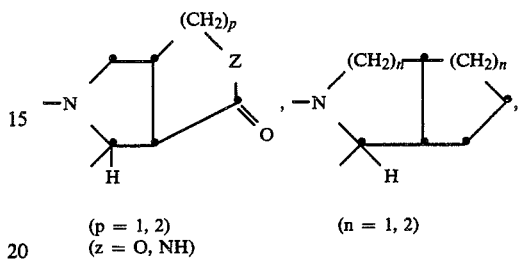

(p = 1, 2)
(z = O, NH)
(n = 1, 2)

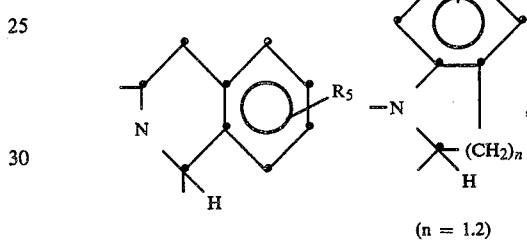

(n = 1,2)

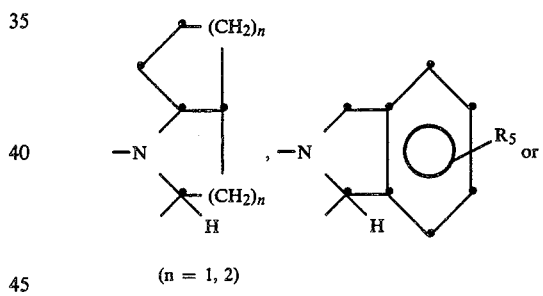

(n = 1, 2)

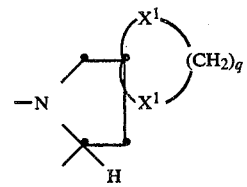

wherein q is 2–4 and $X^1$ is O or S.

(c) dehydro 5-11 membered-N-heterocycle or
(d) heterocycles having the formula

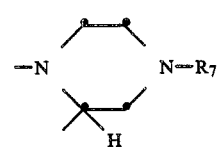

wherein $R_7$ is H, loweralkyl of $C_1-C_8$ or acyl,

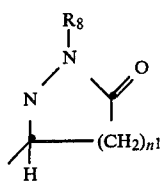

wherein $R_8$ is hydrogen, loweralkyl of $C_1$-$C_8$, aryl of $C_6$-$C_{12}$ substitued aryl of $C_6$-$C_{12}$, arloweralkyl wherein the alkyl is $C_1$-$C_8$ and aryl is $C_6$-$C_{12}$, and, $n^1 = 1$-$3$;

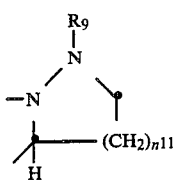

wherein $R_9$ is hydrogen, loweralkyl of $C_1$-$C_8$, aryl of $C_6$-$C_{12}$ substituted aryl of $C_6$-$C_{12}$, arloweralkyl wherein the alkyl is $C_1$-$C_8$ and the aryl is $C_6$-$C_{12}$, and, $n^{11} = 1$-$3$;

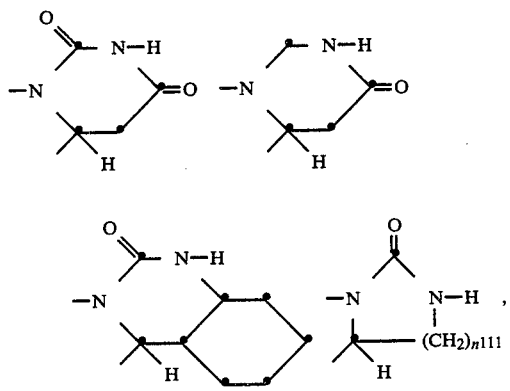

wherein $n^{111} = 1,2$

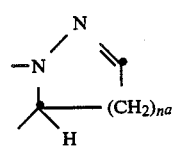

wherein $n^a$ is 1-3,

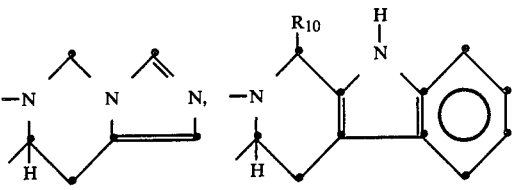

wherein $R_{10}$ is hydrogen, phenyl, hydroxyphenyl or benzyl

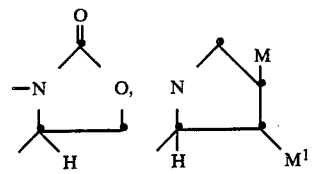

wherein M is OH or loweralkyl or aralkyl, $M^1$ is loweralkyl or aralkyl wherein the alkyl groups are $C_1$-$C_8$ and the aryl groups are $C_6$-$C_{12}$.

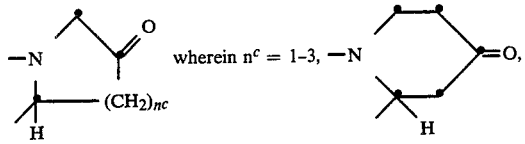

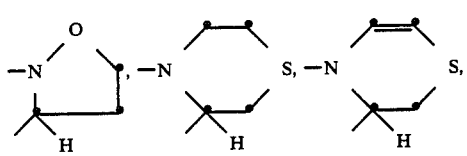

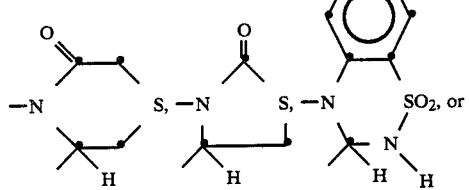

wherein $Q_1$ and $Q_2$ are CO, $CH_2$, S, or O such that only one of $Q_1$ and $Q_2$ can be $CH_2$ and R" is hydrogen, loweralkyl of $C_1$-$C_8$, aryl of $C_6$-$C_{12}$, substituted aryl of $C_6$-$C_{12}$ or arloweralkyl wherein the alkyl is $C_1$-$C_8$ and the aryl is $C_6$-$C_{12}$.

Pharmaceutically acceptable salts are salts of the formula I compounds with various inorganic and organic acids and bases. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like; also salts with organic or inorganic acids such as HCl, HBr, H₂SO₄, H₃PO₄, methanesulfonic acid, toluenesulfonic acid, maleic acid, oxalic acid, fumaric acid, camphorsulfonic acid, acetic acid, pamoic acid, isethionic acid, pivalic acid and the like. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The alkyl substituents recited above denote straight and branched chain hydrocarbons of $C_1$–$C_{12}$ such as methyl, hexyl, propyl, dodecyl isopentyl, isopropyl, neopentyl, etc.

Loweralkyl denotes alkyl groups of $C_1$ to $C_8$ such as ethyl, isobutyl, 4-methylpentyl, and the like.

Alkenyl and alkynyl denote alkyl groups as described above which are modified so that each contains a carbon to carbon double bond or triple bond, respectively, such as vinyl, 2-butenyl, 1-hexynyl, and the like.

Cycloalkyl denotes rings composed of 3 to 10 methylene groups, each which may be substituted or unsubstituted with other hydrocarbon substituents, and include, for example, cyclopentyl, cycloheptyl, 4-methyl cyclohexyl, and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:3:1 octane and spiro 4:4:0 nonane.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms such as, for example, benzyl, phenethyl, 3,3-diphenylpropyl, 3-indolylmethyl, and the like.

Halo means chloro, bromo, iodo, or fluoro.

The aryl substituent represents such groups as phenyl, naphthyl, or biphenyl.

The heteroaryl substituent recited above represents any 5- or 6-membered aromatic ring containing from one to three O, N or S heteroatoms such as, for example, pyridyl, thienyl, furyl, imidazolyl, and thiazolyl; as well as any bicyclic group in which any of the above heterocyclic rings is fused to another aromatic ring such as, for example, indolyl, quinolinyl, isoquinolinyl, benzimidazolyl, benzothiazolyl, benzthienyl, and naphthyridyl.

Acyl denotes aroyl or loweralkanoyl.

The acylamino substituent represents an organic acid derivative such as loweralkanoylamino and aroylamino.

Preferred R groups are H, methyl, ethyl, and benzyl.

Preferred $R_1$ aryl-$(CH_2)_n$- group is phenyl-$(CH_2)_n$- more preferably where n is 2.

Preferred $R_1$ het-$(CH_2)_n$ groups are those where n is 2, and more preferably where het is pyridyl, thienyl, indolyl, imidazolyl, quinolinyl, and isoquinolyl.

The $R_2$ amino lower alkyl moiety is exemplified by groups such as

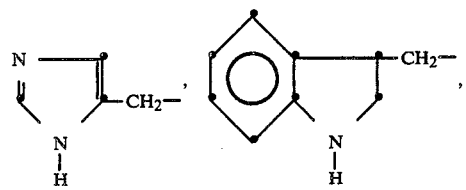

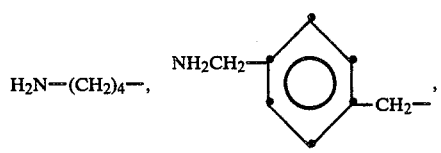

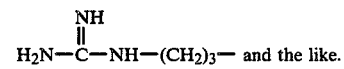

and the like.

Preferred $R_2$ groups are $CH_3$ and $NH_2$—$(CH_2)_4$. Preferred

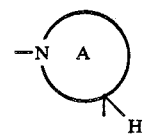

groups include:

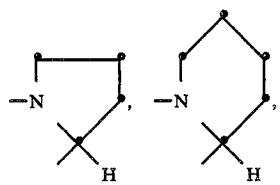

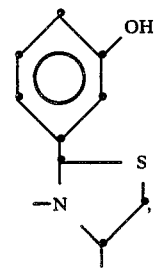

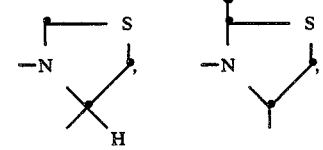

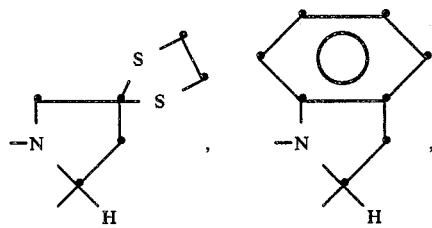

-continued

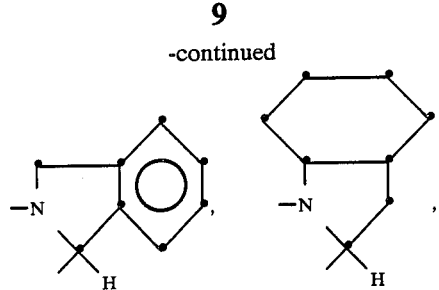

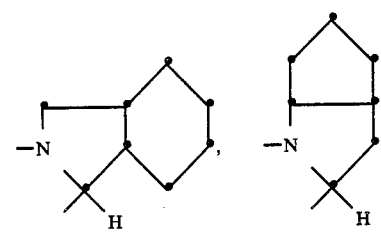

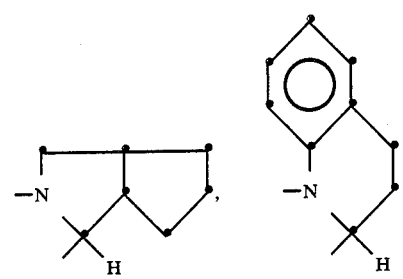

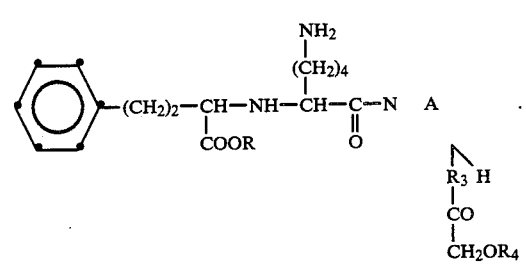

A preferred group of compounds are those having the formula:

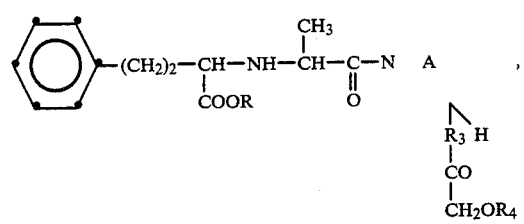

and

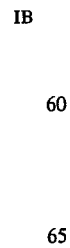

set forth hereinbelow wherein R-R$_4$, n and A are as defined above unless indicated otherwise.

As will be evident to those skilled in the art and as demonstrated in the Examples, reactive groups not involved in the condensations, such as amino, carboxy, mercapto, etc., may be protected by methods standard in peptide chemistry prior to the coupling reactions and subsequently deprotected to obtain the desired products.

Process I

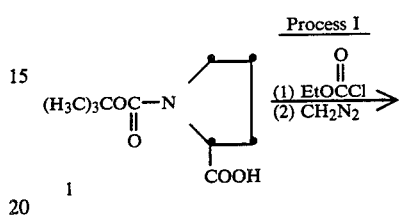

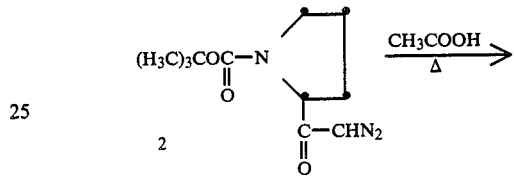

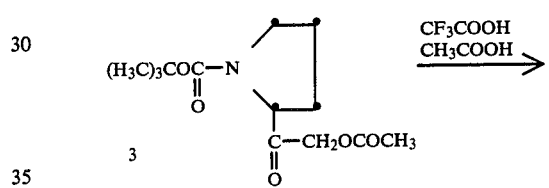

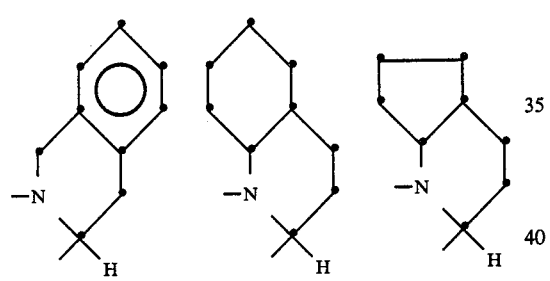

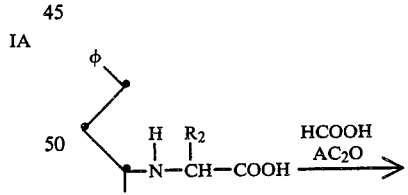

[R = CH$_2$CH$_3$, CH$_2$C$_6$H$_5$; R$_2$ = CH$_3$, (—CH$_2$)$_4$NHCBZ]

4 + 6 ⟶

The products of Formula (I) and the preferred subgroups can be produced by one or more of the processes -continued

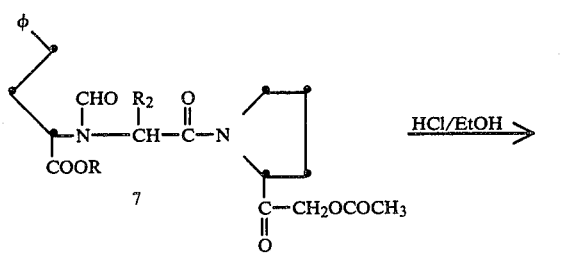

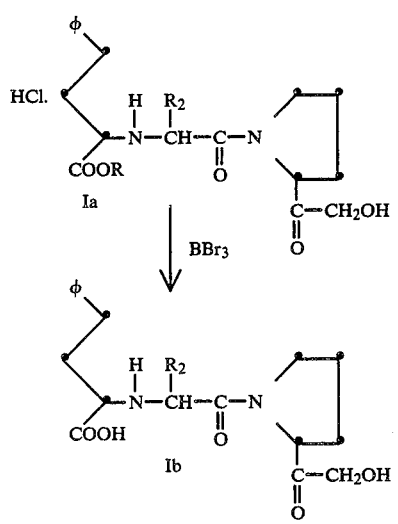

Process II

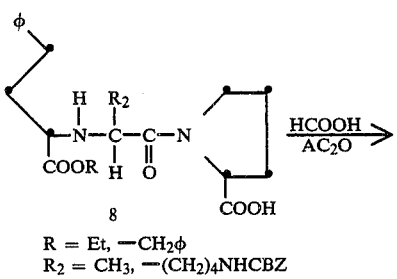

R = Et, —CH₂φ
R₂ = CH₃, —(CH₂)₄NHCBZ

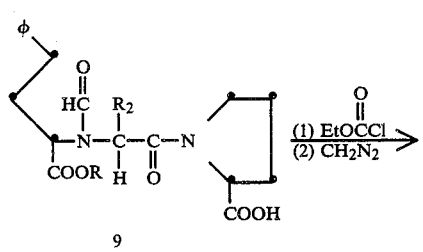

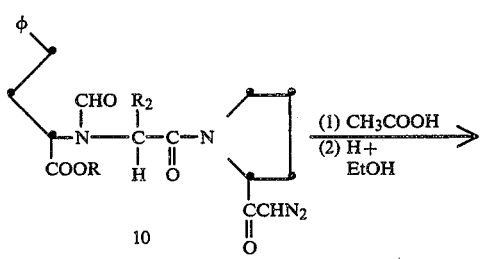

-continued

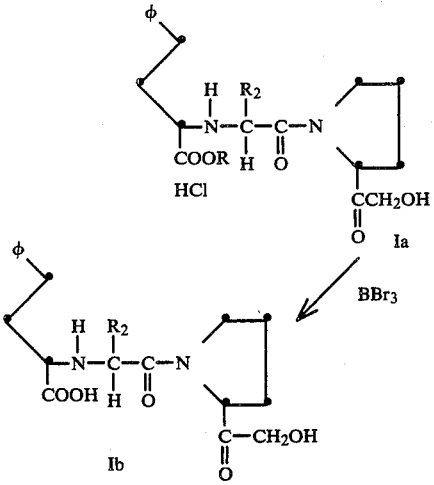

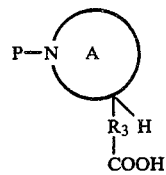

As shown in Process I, an N-protected amino acid; i.e., $$P-N\underset{R_3}{\overset{A}{\bigcirc}}\underset{COOH}{\overset{H}{|}}$$

1

P=a protecting group; e.g., t-butoxycarbonyl, benzyloxycarbonyl, and the like, is converted to the corresponding diazoketone 2 by successive treatment with ethyl chloroformate and diazomethane. Upon brief heating in acetic acid, diazoketone 2 is converted to the corresponding ketol acetate 3. The protecting group, P, is then removed to give acetate 4.

If P=t-butoxycarbonyl, this step is carried out using trifluoroacetic acid and the product is obtained as the CF₃COOH salt. If P=benzyloxycarbonyl, this step is carried out by hydrogenolysis over palladium on charcoal in ethanol-containing acetic acid.

Substituted amino acid 5 is converted to its N-formyl derivative 6 which is then condensed with acetate 4 in CH₂Cl₂ utilizing dicyclohexylcarbodiimide in the presence of 1-hydroxybenztriazole as condensing agent and neutralizing any acid present with, for example, triethylamine to give intermediate 7. The formyl and acetate groups are removed from 7 in dilute alcoholic hydrochloric acid at room temperature to give monoester Ia. Monoester Ia can then be converted to the free acid Ib upon treatment of Ia with boron tribromide in methylene chloride.

In Process II, monoester 8 is converted to the N-formyl compound 9 utilizing the same procedure as in Process I to convert amino acid 5 to N-formyl derivative 6. N-formyl compound 9 is transformed to the diazoketone compound 10 utilizing the same procedure as in Process I to convert the N-protected amino acid 1 to diazoketone 2. Upon heating in acetic acid, diazoketone 10 is converted into ketol acetate intermediate which, upon standing in dilute alcoholic hydrochloric acid, is converted to monoester Ia. Treatment of monoester Ia with boron tribromide gives free acid Ib.

In Processes I and II above, if R₂=loweralkylamino, this amino group can be protected as the benzyloxycarbonyl or related derivative which can subsequently be removed at an appropriate point in the sequence by hydrogenolysis. Similarly, if R₂=benzyl or substituted benzyl, hydrogenolysis can be employed to produce the free acid.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et. al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta,* 206, 136 (1970) in which the hydrolysis of carbobenzyloxy-phenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 104, 646 (1960) or in a high renin rat model such as that of S. Koletsky et. al., *Proc. Soc. Exp. Biol. Med.,* 125, 96 (1967).

Thus, the compounds of the invention are useful in treating hypertension. They are also of value in the management of acute and chronic congestive heart failure, in the treatment of secondary hyperaldosteronism, primary and secondary pulmonary hypertension, renal failure and renal vascular hypertension, and in the management of vascular disorders such as migraine. The application of the compounds of this invention for these and similar disorders will be apparent to those skilled in the art.

In the management of hypertension and those clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 1000 mg. per patient per day which can be administered in single or multiple doses. Preferably, the dosage range will be about 5 to 500 mg. per patient per day; more preferably about 10 to 500 mg. per patient per day.

The compounds of this invention can also be administered in combination with other antihypertensives and-/or diuretics and/or calcuim entry blockers. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methyclothiazide, methyldopa, methyldopate hydrochloride, minoxidil, (S)-1-{[2-(3,4-dimethoxyphenyl)ethyl]amino}-3-{[4(2-thienyl)-1H-imidazol-2-yl]phenoxy}-2-propanol, polythiazide, the pivaloyloxyethyl ester of methyldopa, indacrinone and variable ratios of its enantiomers, nifedipine, verapamil, diltiazem, flumethiazide, bendroflumethiazide, atenolol, (+)-4-{3-{[2-(1-hydroxycyclohexyl)ethyl]-4-oxo-2-thiazolidinyl}propyl}benzoic acid, bumetanide, prazosin, propranolol, *Rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, bepridil, diltiazim, etafenone, fabpamie, felodipine, flunarizine, gallapomie, indapamide, lidoflazine, nicardipine, hifedipine, nimopidine, nitrendipine, perhexiline, prenylamine, tiapamil, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 5-500 milligrams per day range can be effectively combined at levels at the 1-500 milligrams per day range with the following compounds at the indicated per day dose range: hydrochlorothiazide (10-100 mg), timolol (5-60 mg), methyl dopa (65-2000 mg), the pivaloyloxyethyl ester of methyl dopa (30-1000 mg), indacrinone and variable ratios of its enantiomers (25-150 mg) and (+)-4-{3-{[2-(1-hydroxycyclohexyl)ethyl]-4-oxo-2-thiazolidinyl}propyl}-benzoic acid (10-100 mg).

In addition, the triple drug combinations of hydrochlorothiazide (10-100 mg) plus timolol (5-60 mg) plus converting enzyme inhibitor of this invention (1-500 mg) or hydrochlorothiazide (10-100 mg) plus amiloride (5-20 mg) plus converting enzyme inhibitor of this invention (1-500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 500 mg. of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are set forth to illustrate preparation of representative Formula I compounds. Temperatures are in degrees Celsius unless otherwise indicated. All starting materials are known in the literature, are commercially available, or can be made by methods known to those skilled in the art.

EXAMPLE 1

(S)-1-t-Butoxycarbonyl-2-(2-diazo-1-oxoethyl)pyrrolidine

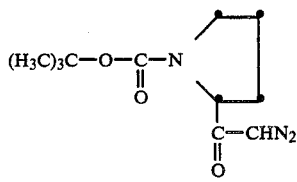

To a stirred solution of (L)-t-butoxycarbonylproline (5.4 g; 2.5 mmol) in ether (50 ml) and triethylamine (3.5 ml) at $-10°$ there was added dropwise ethyl chloroformate (1.93 ml) in ether (2 ml). The precipitated triethylamine HCl was filtered and to the stirred filtrate at $-5°$ there was added diazomethane in ether (80 ml ethereal diazomethane-prepared from 10 g of N-methyl-N-nitrosourea). The mixture was kept at $-5°$ for 18 hour, concentrated to dryness and the residue dissolved in ethyl acetate. The latter solution was extracted with aqueous KHCO$_3$, saturated aqueous NaCl, dried over Na$_2$SO$_4$ and concentrated to dryness to give (S)-1-t-butoxycarbonyl-2-(2-diazo-1-oxoethyl)-pyrrolidine [5.14 g; NMR (CDCl$_3$)δ5.43

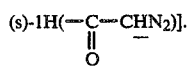

Alternatively, (L)-benzyloxycarbonylproline may be utilized as starting material.

EXAMPLE 2

(S)-1-t-Butoxycarbonyl-2-(2-acetoxy-1-oxoethyl)pyrrolidine

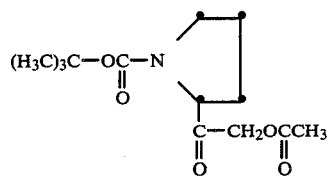

A solution of 1.00 g of the diazoketone product of Example 1 in acetic acid (15 ml) was refluxed for 10 minutes. The mixture was cooled, filtered and the acetic acid removed under reduced pressure to give (S)-1-t-butoxycarbonyl-2-(2-acetoxy-1-oxoethyl)-pyrrolidine, which was purified by chromatography on silica gel eluting with 3:1-hexane; ethyl acetate (R$_f$=0.3).

EXAMPLE 3

(S)-2-(2-Acetoxy-1-oxoethyl)-pyrrolidine trifluoracetate

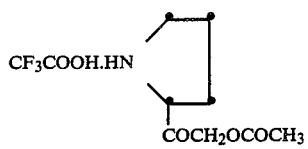

A solution of 1.00 g of the product of Example 2 can be kept in 10 ml of 1:1 trifluoracetic acid-acetic acid at 20° for 30 minutes. The solvents can then be removed under reduced pressure to give (S)-2-(2-acetoxy-1-oxoethyl)-pyrrolidine trifluoracetate.

If (L) benzyloxycarbonylproline is used as the starting material, for Example 1, the benzyloxycarbonyl group can be removed by hydrogenolysis over 10% palladium on charcoal in ethanol containing acetic acid [procedure of P. G. Katsoyannis and G. P. Schwartz, *Methods in Enzymology*, 47, 547 (1974)].

EXAMPLE 4

N-Formyl,N-(1-carbethoxy-3-phenylpropyl)(L)-alanine

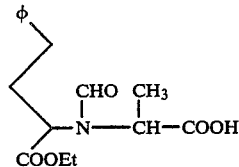

To a stirred solution of 558 mg (2.00 mmol) of N-(1-carbethoxy-3-phenylpropyl)(L)-alanine in 5 ml of 98-100% formic acid at 0° there can be added acetic anhydride (1.5 ml). After 4 hours at 0°, iced water (2 ml) can be added dropwise and the mixture concentrated under reduced pressure to give N-formyl, N-(1-carbethoxy-3-phenylpropyl)(L)-alanine.

Alternatively, N-(1-carbobenzyloxy-3-phenylpropyl)(L)alanine may be utilized as the starting material yielding N-formyl, N-(1-carbobenzyloxy-3-phenylpropyl)(L)-alanine which can be utilized in Examples 5, 6 and 7 below.

EXAMPLE 5

N-Formyl, N-(1-carbethoxy-3-phenylpropyl(L)-alanyl (S)-2-(2-acetoxy-1-oxoethyl)-pyrrolidine

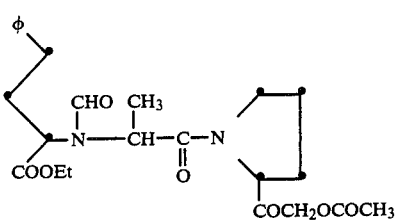

To a stirred solution at 0° of (S)-2-(2-acetoxy-1-oxoethyl)-pyrrolidine trifluoracetate (570 mg; 2 mmol) and triethylamine (202 mg; 2 mmol) in 10 ml of $CH_2Cl_2$ there can be added N-formyl-N-(1-carbethoxy-3-phenylpropyl(L)-alanine (558 mg; 2 mmol) followed by 1-hydroxybenztriazole (270 mg; 2 mmol) and dicyclohexylcarbodiimide (430 mg; 2.1 mmol). The mixture can then be stirred at 0° for 18 hours, then filtered, and the precipitate washed with $CH_2Cl_2$. The combined filtrate and washes can be washed with dilute HCl dilute $NaHCO_3$, saturated aqueous NaCl, dried over $Na_2SO_4$ and concentrated to give N-formyl, N-(1-carbethoxy-3-phenylpropyl(L)-alanyl(S)-2-(2-acetoxy-1-oxoethyl)-pyrrolidine.

EXAMPLE 6

N-(1-Carbethoxy-3-phenylpropyl)(L)-alanyl(S)-2-(2-hydroxy-1-oxoethyl)-pyrrolidine hydrochloride

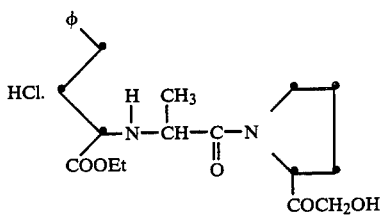

A solution of N-formyl, N-(1-carbethoxy-3-phenylpropyl)(L)-alanyl(S)-2-(2-acetoxy-1-oxoethyl)-pyrrolidine (460 mg; 1 mmol) in 5 ml of 5% ethanolic hydrochloric acid (5.5 ml of 38% aqueous HCl in 60 ml of ethanol) can be kept at 25° for 2 days. It can then be concentrated under reduced pressure and the residue triturated with ether to give N-(1-carbethoxy-3-phenylpropyl)(L)-alanyl (S)-2-(2-hydroxy-1-oxoethyl)-pyrrolidine hydrochloride.

EXAMPLE 7

N-(1-carboxy-3-phenylpropyl)(L)-alanyl-(S)-2-(2-hydroxy-1-oxoethyl)-pyrrolidine

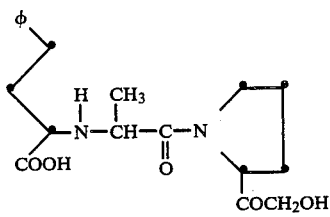

The ethyl ester group can be removed from the product of Example 6 by treatment with boron tribromide in $CH_2Cl_2$ utilizing the procedure of A. M. Felix, *J. Org. Chem.*, 39, 1427 (1974).

If the benzyl ester is utilized in this sequence, it can be removed by hydrogenolysis as described in Example 13 hereinafter.

EXAMPLE 8

N-Formyl,N(1-carbethoxy-3-phenylpropyl)(L)-alanyl (L)proline

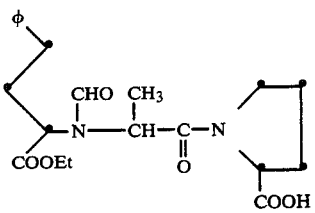

Utilizing the procedure of Example 4, N(1-carbethoxy-3-phenylpropyl)(L)alanyl(L)proline can be converted to the corresponding N-formylderivative.

N(1-carbobenzyloxy-3-phenylpropyl)(L)alanyl (L)proline may be similarly utilized in this Example as well as in Examples 9 and 10 which follow.

EXAMPLE 9

N-Formyl,N(1-carbethoxy-3-phenylpropyl(1)-alanyl(S)-2-(2-diazo-1-oxoethyl)-pyrrolidone

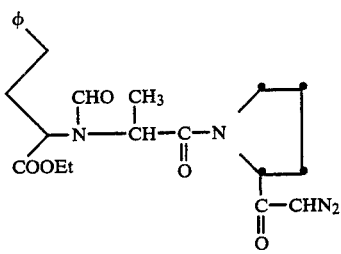

Utilizing the procedure of Example 1, N-formyl, N-(1-carbethoxy-3-phenylpropyl)(L)-alanyl L-proline can be converted into the corresponding diazoketone.

EXAMPLE 10

N(1-Carbethoxy-3-phenylpropyl)(L)-alanyl(S)-2-(2-hydroxy-1-oxoethyl)pyrrolidine hydrochloride

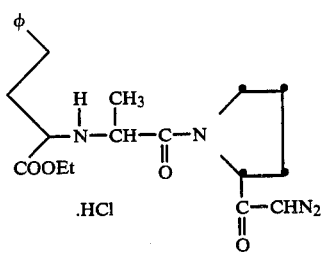

Utilizing the procedure of Example 6, N-formyl, N(1-carbethoxy-3-phenylpropyl)(L)-alanyl (S)-2(2-diazo-1-oxoethyl)-pyrrolidine can be converted into the title product; namely, N(1-carbethoxy-3-phenylpropyl)(L)alanyl(S)-2-(2-hydroxy-1-oxoethyl)pyrrolidine hydrochloride.

EXAMPLE 11

Nα-Formyl,Nα-(1-carbobenzyloxy-3-phenylpropyl), Nε-CBZ-(L)-lysine

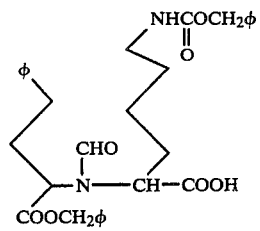

Utilizing the procedure of Example 4, Nα-(1-carbobenzyloxy-3-phenylpropyl), Nε-CBZ-(L) lysine can be converted into the corresponding title Nα-formyl derivative.

EXAMPLE 12

Nα-Formyl,Nα-(1-carbobenzyloxy-3-phenylpropyl),Nε-CBZ-(L)-lysyl-(S)-2-(2-acetoxy-1-oxoethyl)-pyrrolidine

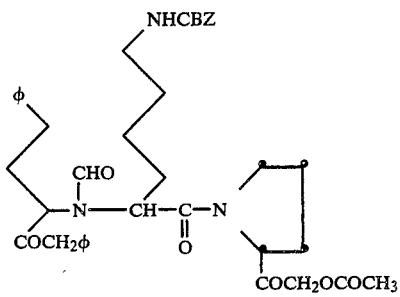

Utilizing the procedure of Example 5, the product of Example 11 can be condensed with (S)-2-(2-acetoxy-1-oxoethyl)pyrrolidine trifluoracetate to give the corresponding dipeptide derivative, Nα-formyl,Nα-(1-carbobenzyloxy-3-phenylpropyl),Nε-CBZ-(L)-lysyl(S)-2-(2-acetoxy-1-oxoethyl)-pyrrolidine.

EXAMPLE 13

Nα-(1-Carboxy-3-phenylpropyl)-(L)-lysyl-(S)-2-(2-hydroxy-1-oxoethyl)-pyrrolidinedihydrochloride

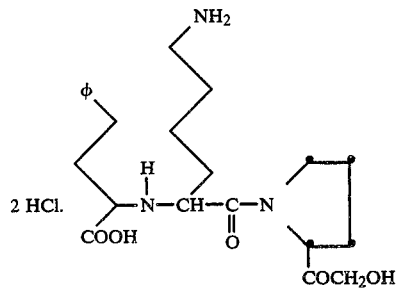

Utilizing the procedure of Example 6, the formyl and acetate groups can be removed from the product of Example 12. The Nε-CBZ and benzyl ester groups can then be removed by hydrogenolysis in ethanol containing two equivalents of hydrochloric acid over 10% palladium on charcoal [procedure of P. G. Katsoyannis and G. P. Schwartz, Methods in Enzymology, 47, 547 (1974)] to obtain the title compound.

EXAMPLE 14

Additional proline surrogates, of the general structure

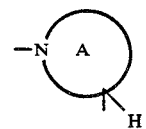

or protected versions thereof can be coupled with protected amino acid derivatives having the general formula

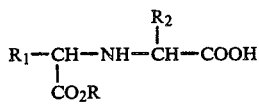

particularly derivatives of L-lysine and L-alanine, by the procedures of Examples 5, 6 and 7 to afford the products of Formula I. In general, the ε-amino function of products derived from L-lysine remain protected until the final compound of Formula I has been obtained.

Proline surrogates with acetic acid and propionic acid side chains; e.g., pyrrolidine-2-acetic acid (homoproline), can be similarly utilized in the above procedures.

What is claimed is:

1. A compound having the formula:

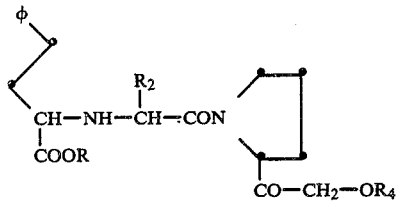

wherein:
R is hydrogen, ethyl, benzyl;
$R_2$ is methyl, $(CH_2)_4NH_2$;
$R_4$ is hydrogen, $COCH_3$; and, the pharmaceutically acceptable salts thereof.

2. A compound having the formula:

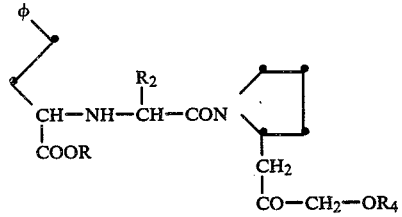

wherein:
R is hydrogen, ethyl, benzyl;
$R_2$ is methyl, $(CH_2)_4NH_2$;
$R_4$ is hydrogen, $COCH_3$; and
the pharmaceutically acceptable salts thereof.

3. A pharmaceutical composition for treating hypertension comprising a pharmaceutically acceptable carrier and an antihypertensively effective amount of a compound of claim 1 or claim 2.

4. A method of treating hypertension in humans which comprises administering to a person in need of such treatment an antihypertensively effective amount of a compound of claim 1 or claim 2.

* * * * *